US012396975B2

(12) United States Patent
Lindberg (10) Patent No.: US 12,396,975 B2
(45) Date of Patent: Aug. 26, 2025

(54) TREATMENT OF AL AMYLOIDOSIS WITH MELFLUFEN

(71) Applicant: Oncopeptides AB, Stockholm (SE)

(72) Inventor: Jakob Lindberg, Stockholm (SE)

(73) Assignee: Oncopeptides AB, Stockholm (SE)

( * ) Notice: Subject to any disclaimer, the term of this patent is extended or adjusted under 35 U.S.C. 154(b) by 921 days.

(21) Appl. No.: 17/600,657

(22) PCT Filed: Apr. 3, 2020

(86) PCT No.: PCT/EP2020/059641
§ 371 (c)(1),
(2) Date: Oct. 1, 2021

(87) PCT Pub. No.: WO2020/201542
PCT Pub. Date: Oct. 8, 2020

(65) Prior Publication Data
US 2022/0193019 A1    Jun. 23, 2022

(30) Foreign Application Priority Data

Apr. 3, 2019 (GB) ...................................... 1904714
Dec. 6, 2019 (GB) ...................................... 1917908

(51) Int. Cl.
*A61K 31/223* (2006.01)
*A61K 31/573* (2006.01)
(52) U.S. Cl.
CPC .......... *A61K 31/223* (2013.01); *A61K 31/573* (2013.01)
(58) Field of Classification Search
CPC ............................ A61K 31/573; A61K 31/223
See application file for complete search history.

(56) References Cited

U.S. PATENT DOCUMENTS

2022/0047507 A1* 2/2022 Lindberg ............... A61K 47/26

FOREIGN PATENT DOCUMENTS

| WO | 2001/096367 A1 | 12/2001 |
| WO | 2012/146625 A1 | 11/2012 |
| WO | 2014/065751 A1 | 5/2014 |
| WO | 2017/093443 A1 | 6/2017 |

OTHER PUBLICATIONS

American Journal of Hematology, vol. 89, No. 12, Dec. 2014 (Year: 2014).*
Wickstrom (Oncotarget, 2017, vol. 8, (No. 39), pp. 66641-66655) (Year: 2017).*
International Search Report and Written Opinion issued Jul. 13, 2020 in PCT/EP2020/059641.
Brennan et al., 2018 "Generation of Luciferase-expressing Tumor Cell Lines" Bio-Protocol 8(8) 2817.
Dietrich et al., 2010 "Treatment with intravenous melphalan and dexamethasone is not able to overcome the poor prognosis of patients with newly diagnosed systemic light chain amyloidosis and severe cardio involvement" Blood 116(4): 522-528.
Gertz et al., 2005 "Definition of Organ Involvement and Treatment Response in Immunoglobulin Light Chain Amyloidosis (AL): A Consensus Opinion From the 10th International Symposium on Amyloid and Amyloidosis" American Journal of Hematology 79:319-328.
Gertz et al., 2016 "Stem Cell Transplantation Compared With Melphalan Plus Dexamethasone in the Treatment of Immunoglobulin Light-Chain Amyloidosis" Cancer 122:2197-2205.
Jaccard et al., 2007 "High-Dose Melphalan versus Melphalan plus Dexamethasone for AL Amyloidosis" The New England Journal of Medicine 357 (11): 1083-1093.
Kyle et al., 1997 "A Trial of Three Regimens for Primary Amyloidosis: Colchicine Alone, Melphalan and Prednisone, and Melphalan, Prednisone, and Colchicine" The New England Journal of Medicine 336(17):1202-1207.
Lebovic et al., 2008 "Predictors of survival in patients with systemic light-chain amyloidosis and cardiac involvement initially ineligible for stem cell transplantation and treated with oral melphalan and dexamethasone" Br. J. Haematol 143(3): 369-373.
Mateos et al., 2017 "Melflufen Therapy for Relapsed Refractory Multiple Myeloma (RRMM) Patients Refractory to Daratumumab and/or Pomalidomide: A Report on Early Efficacy" Blood 130 (Supplement 1) 1841.
Paba-Prada et al., 2014 "Determination of the MTD and Encouraging Results in an Ongoing Open-Label Phase 1/2a Study of the Safety and Efficacy of Melflufen and Dexamethasone in Combination for Patients with Relapsed and Relapsed-Refractory Multiple Myeloma (RRMM)" Blood 124(21):2123.
Palladini et al., 2004 "Association of melphalan and high-dose dexamethasone is effective and well tolerated in patients with AL (primary) amyloidosis who are ineligible for stem cell transplantation" Blood 103(8):2936-2938.
Palladini et al., 2019 "OP201: A Phase 1/2 Study of Melflufen and Dexamethasone in Patients with Immunoglobulin Light Chain (AL) Amyloidosis" Blood 134 (Supplement 1) 3163.
Palladini et al., 2014 "Oral melphalan and dexamethasone grants extended survival with minimal toxicity in AL amyloidosis: long-term results of a risk-adapted approach" Haematologica 99(4):743-750.

(Continued)

*Primary Examiner* — Kortney L. Klinkel
*Assistant Examiner* — Richard Grant Peckham
(74) *Attorney, Agent, or Firm* — Biospark Intellectual Property Law (57) ABSTRACT

The invention provides melflufen, or a salt thereof, or a pharmaceutical formulation comprising melflufen, or a salt thereof, for use in the treatment and/or prophylaxis of immunoglobulin light chain (AL) amyloidosis. The invention also provides dosage regimens and kits that find utility in the treatment and/or prophylaxis of AL amyloidosis, and methods for the treatment and/or prophylaxis of AL amyloidosis, and uses of melflufen, or a salt thereof, for the manufacture of a medicament for the treatment of AL amyloidosis.

19 Claims, 8 Drawing Sheets

(56) References Cited

OTHER PUBLICATIONS

Pour et al., 2018 "The OP-104 Anchor Study: A Phase 1/2 Study of Safety and Efficacy of Melflufen and Dexamethasone in Combination with Either Bortezomib or Daratumumab in Patients with Rrmm; First Report on Phase 1 Data" Blood 132 (Supplement 1) 1967.
Skinner et al., 1996 "Treatment of 100 Patients with Primary Amyloidosis: A Randomized Trail of Melphalan, Prednisone, and Colchicine Versus Colchicine Only" Am. J. Med. 100(3):290-298.
Wechalekar et al., 2015 "Guidelines on the management of AL amyloidosis" Br. J. Haematol. 168(2):186-206.

* cited by examiner

TREATMENT OF AL AMYLOIDOSIS WITH MELFLUFEN

FIELD OF THE INVENTION

The present invention relates to the treatment and/or prophylaxis of immunoglobulin light chain (AL) amyloidosis. The present invention also relates to dosage regimens and kits that find utility in the treatment and/or prophylaxis of AL amyloidosis.

BACKGROUND OF THE INVENTION

Immunoglobulin light chain (AL) amyloidosis is a debilitating and terminal disease caused by the accumulation of amyloid fibrils. In AL amyloidosis the amyloid fibrils are formed from aggregated immunoglobulin light chains originating from abnormal bone marrow plasma cells. The accumulation of amyloid fibrils in vital organs can lead to progressive organ failure. Depending on the degree of organ involvement, the life expectancy of a patient suffering from AL amyloidosis can be significantly reduced. For example, life expectancy for an AL amyloidosis patient with severe cardiomyopathy can range from a few years to less than 6 months (Jaccard et al. 2007, N Engl J Med, 357(11), 1083-93).

The currently-available treatments for AL amyloidosis are based on anti-myeloma therapies that reduce or eliminate the abnormal bone marrow plasma cells, thus reducing the formation of amyloid fibrils formed from aggregated immunoglobulin light chains. A first line treatment for AL amyloidosis is melphalan, which is typically used in combination with a steroid. For example, the administration of melphalan (for example, 20-25 mg/m$^2$ of body surface area) in combination with prednisolone has been shown to reduce plasma cell levels and increase survival rates by a few months (Kyle et al. 1997, N Engl J Med, 336(17), 1202-7, and Skinner et al. 1996, Am J Med, 100(3), 290-298). Later studies have also reported that standard doses of melphalan in combination with dexamethasone is also effective for the treatment of AL amyloidosis (Palladini et al, 2004, Blood, 103(8), 2936-8, Lebovic et al, 2008, Br J Haematol, 143(3), 369-73, and Dietrich et al 2010, Blood, 116(4), 522-8).

"High-dose" melphalan (for example, 200 mg/m$^2$ of body surface area) with autologous hematopoietic stem cell rescue has also shown promise in treating AL amyloidosis (Jaccard et al. 2007). The high dose of melphalan is used to ablate the plasma cell levels of the patient, which are then restored by the transplantation of hematopoietic stem cells. A major problem with this treatment is the significant treatment-related toxicity and high treatment related mortality rates (Wechalekar et al, 2015, Br J Haematol, 168(2), 186-206).

Further therapies that have shown promise for the treatment of AL amyloidosis include the protease inhibitor, bortezomib, and the immunomodulatory drugs, thalidomide and lenalidomide (Wechalekar et al, 2015).

A major limitation with the currently-available treatments is that the clinical benefit does not occur for many months after treatment. In addition, AL amyloidosis patients often experience significant treatment-related toxicity from melphalan based therapies. The increased toxicity experienced in AL amyloidosis patients means that there is a compromise between using a dose that is high enough to provide a clinical benefit for the patient whilst avoiding a dose that has intolerable toxic side effects. There is therefore a significant need for more effective treatments. In particular, there is a need for safe treatments that provide clinical benefits for the AL amyloidosis patient, whilst also displaying manageable side-effects.

SUMMARY OF THE INVENTION

The present invention provides melflufen, and salt(s) thereof, for use in the treatment and/or prophylaxis of immunoglobulin light chain (AL) amyloidosis.

The present invention further provides a method for the treatment and/or prophylaxis of AL amyloidosis, comprising the step of administering melflufen, or a salt thereof, to a patient with AL amyloidosis or a patient at risk of developing AL amyloidosis.

The present inventors have found that melflufen, and salts thereof, are surprisingly effective for the treatment and prophylaxis of AL amyloidosis. In particular, the present inventors have found that melflufen is highly cytotoxic in an in vitro AL amyloidosis cell model using plasma cells obtained from patients afflicted with the condition. The present inventors postulate that the surprisingly high potency of melflufen will allow for the use of therapeutically effective doses that are safer and more effective than existing AL amyloidosis treatments.

Melflufen thus provides a novel treatment that is more effective and safer than existing AL amyloidosis treatments.

In preferred embodiments of the invention, the melflufen, or salt thereof is administered in a dose of about 15 to 150 mg (excluding the mass of any counterion), preferably a dose of 35 to 45 mg (excluding the mass of any counterion). Preferably, the melflufen, or salt thereof, is administered simultaneously, sequentially or separately with a steroid, for example selected from prednisone, prednisolone and dexamethasone. Preferably, the melflufen, or salt thereof, is administered simultaneously, sequentially or separately with dexamethasone.

The doses and dosage regimens of the present invention are particularly well-tolerated and they are effective in the treatment and/or prophylaxis of AL amyloidosis.

The invention also provides the use of melflufen, or a salt thereof, for the manufacture of a medicament for the treatment and/or prophylaxis of AL amyloidosis.

The present invention further provides a kit comprising melflufen and a steroid, for example selected from prednisone, prednisolone and dexamethasone. Preferably, the steroid is dexamethasone. The kit of the present invention finds use in the treatment and/or prophylaxis of AL amyloidosis.

DETAILED DESCRIPTION

The inventors of the present invention have found that melflufen is surprisingly effective for the treatment and/or prophylaxis of AL amyloidosis.

AL amyloidosis is characterised by the aggregation of immunoglobulin light chains to form amyloid fibrils. The accumulation of the amyloid fibrils in vital organs leads to organ failure. Depending on the degree of organ involvement, the life expectancy of a patient suffering from AL amyloidosis can be significantly reduced.

Currently-available treatments for AL amyloidosis are limited in their efficacy due to high treatment-related toxicity and poor response rates. A first line of treatment for AL amyloidosis is melphalan. Various treatment regimens using melphalan have been described. For example, the administration of a standard-dose of melphalan (for example, 10-20 mg/m$^2$ of body surface area) in combination with prednisolone or dexamethasone, and high-dose melphalan (for example, 200 mg/m$^2$ of body surface area) with autologous hematopoietic stem cell rescue (Jaccard et al., 2007 and Wechalekar et al, 2015). A major limitation with these treatments are the high levels of treatment-related toxicity and poor response rates.

As discussed in more detail below, the present inventors have surprisingly found that melflufen is highly cytotoxic in an in vitro AL amyloidosis cell model. In cell samples obtained from a population of AL amyloidosis patients, $EC_{50}$ values as low as 1 nM were observed for melflufen. The surprisingly high potency of melflufen is expected to allow the use of therapeutically effective doses that are safer and more effective in the treatment and/or prophylaxis of AL amyloidosis compared to existing treatments.

Notably, the inventors have found that melflufen is at least 100 times more cytotoxic than melphalan in the in vitro AL amyloidosis cell model.

Melflufen and Salts Thereof

Melflufen (also known as melphalan flufenamide and L-Melphalanyl-4-fluoro-L-phenylalanine ethyl ester), is an anti-tumour agent useful in the treatment cancer, particularly the treatment of multiple myeloma. Melflufen, and salts thereof, especially the hydrochloride salt thereof, are known from, for example, WO 01/96367 and WO 2014/065751. The structure of the hydrochloride salt of melflufen is shown below:

For the avoidance of doubt, in this document, when the term "melflufen" is used, it includes isotopic derivatives of melflufen, unless stated otherwise.

Also for the avoidance of doubt, when referred to in this document, the mass of melflufen is the mass of the melflufen molecule excluding the mass of any counterion unless explicitly stated otherwise.

Salts of melflufen which are suitable for use in the present invention are those wherein a counterion is pharmaceutically acceptable. Suitable salts include those formed with organic or inorganic acids. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_1$-$C_4$) alkyl or aryl sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxalic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine.

Preferred salts of melflufen include acid addition salts such as those formed from hydrochloric, hydrobromic, acetic, p-toluenesulfonic, tartaric, sulphuric, succinic, phosphoric, oxalic, nitric, methanesulfonic, malic, maleic and citric acid. More preferably, the salt of melflufen for use according to the present invention is the hydrochloride salt (i.e. the addition salt formed from hydrochloric acid).

Those skilled in the art of organic chemistry will appreciate that many organic compounds can form complexes with solvents in which they are reacted or from which they are precipitated or crystallized. These complexes are known as "solvates". For example, a complex with water is known as a "hydrate". The complex may incorporate a solvent in stoichiometric or non-stoichiometric amounts. Solvates are described in Water-Insoluble Drug Formulation, 2$^{nd}$ ed R. Lui CRC Press, page 553 and Byrn et al Pharm Res 12(7), 1995, 945-954. Before it is made up in solution, the melflufen, or a salt thereof, for use in the present invention may be in the form of a solvate. Solvates of melflufen that are suitable for use according to the present invention are those wherein the associated solvent is pharmaceutically acceptable. For example a hydrate is a pharmaceutically acceptable solvate.

Formulations

While it is possible for melflufen, and salts thereof, to be administered alone, it is preferable for it to be present in a formulation and particularly in a pharmaceutical formulation. Pharmaceutical formulations include those suitable for oral, parenteral (including subcutaneous, intradermal, intraosseous infusion, intramuscular, intravascular (bolus or infusion), and intramedullary), intraperitoneal, transmucosal, transdermal, rectal and topical (including dermal, buccal, sublingual and intraocular) administration although the most suitable route may depend upon, for example, the condition and disorder of the subject under treatment.

In one embodiment of the invention, melflufen is administered as a pharmaceutical formulation suitable for oral or parenteral (including subcutaneous, intradermal, intraosseous infusion, intramuscular, intravascular (bolus or infusion), and intramedullary) administration.

Pharmaceutical formulations of melflufen suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The melflufen may also be presented as a bolus, electuary or paste. Various pharmaceutically acceptable carriers and their formulation are described in standard formulation treatises, e.g., Remington's Pharmaceutical Sciences by E. W. Martin. See also Wang, Y. J. and Hanson, M. A., Journal of Parenteral Science and Technology, Technical Report No. 10, Supp. 42:2S, 1988.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. Preferably, the formulations may be presented in unit dosage or divided dosage containers, for example sealed ampoules and vials. The formulation may be stored in a freeze-dried (lyophilised) condition requiring only the addition of the sterile liquid carrier, for example saline, a physiologically acceptable solution or water-for-injection, immediately prior to use.

Extemporaneous injection and infusion solutions and suspensions may be prepared from sterile powders, granules or other dry composition. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

In a preferred embodiment of the invention, the melflufen for use in the present invention comprises a lyophilized pharmaceutical preparation of melflufen or a salt thereof. The term "lyophilized pharmaceutical preparation of melflufen or a salt thereof" is understood to mean that the melflufen or salt thereof is freeze-dried ("lyophilization", "lyophilized" etc. may in the present context be used interchangeably with "freeze-drying", "freeze-dried" etc.). A lyophilized pharmaceutical preparation of melflufen or a salt thereof as described herein may be a white, fluffy powder in contrast to a non-lyophilized melflufen or a pharmaceutically acceptable salt thereof, which is typically in the form of a dense, slightly yellowish powder.

A lyophilized pharmaceutical preparation of melflufen, or a salt thereof, for use in the present invention may comprise at least one excipient selected from the group comprising a polysorbate; a polyethylene glycol; β-cyclodextrin; α-cyclodextrin; hydroxypropyl-β-cyclodextrin; sulfobutylether-3-cyclodextrin; lactose; benzyl alcohol; disodium succinate; propylene glycol; cremophor EL; dimethyl sulfoxide; D-mannitol; trehalose; sucrose and an amino acid (and in particular an excipient selected from the group comprising β-cyclodextrin; α-cyclodextrin; hydroxypropyl-β-cyclodextrin; sulfobutylether-3-cyclodextrin; trehalose; and sucrose).

In one embodiment, a lyophilized pharmaceutical preparation of melflufen, or a salt thereof, for use in the present invention may comprise sucrose. The inclusion of sucrose provides a lyophilized preparation that is stable as such, and water-soluble, without the presence of an organic solvent, at a sufficient rate compared to the degradation rate, and is thereby useful in therapy and does not have toxicity brought about by the organic solvent. Due to the increased solubility and/or rate of dissolution of melflufen, or a salt thereof, after lyophilization in the presence of sucrose, it is possible to prepare a dissolved melflufen, or a salt thereof, solution, such as a pharmaceutical composition comprising melflufen, or a salt thereof, which has a usefully high concentration of melflufen and which is substantially free from organic solvents.

Preparation of a lyophilized pharmaceutical preparation, a lyophilized pharmaceutical composition, and a kit for making such compositions, of melflufen or a salt thereof, is described in detail in WO 2012/146625 and WO 2014/065741, the contents of which are incorporated herein by reference.

A pharmaceutical formulation of melflufen, or a salt thereof, for use in the present invention may comprise a lyophilized pharmaceutical preparation comprising melflufen, or a salt thereof. In certain embodiments, the formulation comprises sucrose. For example, the formulation comprises sucrose with a weight ratio (w/w) between melflufen and sucrose of about 1:25 to 1:75, for example 1:50.

Where the formulation is a pharmaceutical solution, it may be prepared from a lyophilized pharmaceutical preparation comprising melflufen, or a salt thereof, and further comprise a physiologically acceptable solvent(s), such as a glucose solution and/or a saline solution.

It should be understood that in addition to the ingredients particularly mentioned above, the formulations for use in this invention may include other agents conventional in the art having regard to the type of formulation in question.

Dosage Regimens

Melflufen, or a salt(s) thereof, and pharmaceutical formulations comprising melflufen, find use in the treatment and/or prophylaxis of AL amyloidosis.

The effectiveness of melflufen, and salts thereof, in the treatment and prophylaxis of AL amyloidosis may be assessed according to the guidelines set out in Gertz et al., Am J Hematol, 2004. 79, 319-328. A positive clinical response may be characterized by the improvement of organ function known to be affected by amyloid fibrils. A positive response to the treatment may also be characterized by a hematological response to the treatment. A positive hematological response may be defined as the reduction or complete disappearance of immunoglobulin or light chains in serum or urine samples obtained from the patient. Melflufen, and salts thereof, are effective in producing a positive clinical response in patient afflicted with AL amyloidosis or at risk of developing AL amyloidosis.

The amount of melflufen which is required to achieve a therapeutic effect will vary with particular route of administration and the characteristics of the subject under treatment, for example the species, age, weight, sex, medical conditions, the particular disease and its severity, and other relevant medical and physical factors. An ordinarily skilled physician can readily determine and administer the effective amount of melflufen required for treatment and/or prophylaxis of AL amyloidosis.

Melflufen may be administered daily, every second or third day, weekly, every second, third or fourth week or even as a high single dose depending on the subject and severity of the AL amyloidosis to be treated.

In one embodiment of the invention, the melflufen, or salt thereof, may be administered in an amount of about 15 to 150 mg (excluding the mass of any counterion). For example, 15, 20, 25, 40, 50, 60, 70, 80, 90, 100, 110, 120, 130, 140 or 150 mg (excluding the mass of any counterion). Preferably, the dosage of melflufen or salt thereof, per administration is 25 to 75 mg (excluding the mass of any counterion). More preferably, the dosage of melflufen or salt thereof, per administration is 35 to 45 mg (excluding the mass of any counterion). In another preferred embodiment, the dosage of melflufen or salt thereof, per administration is 20 to 40 mg (excluding the mass of any counterion), for example 20, 30 or 40 mg. In another preferred embodiment, the dosage of melflufen or salt thereof, per administration is 15 to 35 mg (excluding the mass of any counterion), and more preferably 20 to 30 mg, for example 20, 25 or 30 mg.

In another preferred embodiment, the dosage of melflufen or salt thereof, per administration is 15 to 25 mg (excluding the mass of any counterion), for example 20 mg. In another preferred embodiment, the dosage of melflufen or salt thereof, per administration is 25 to 35 mg (excluding the mass of any counterion), for example 30 mg.

In another embodiment of the invention, the melflufen, or salt thereof, may be administered in a single high dose. A single high dose may be about 150 to 800 mg. For example, 150, 200, 300, 400, 500, 600, 700 and 800 mg (excluding the mass of any counterion) in a single dose.

In another embodiment of the invention, the melflufen, or salt thereof, is used together with hematopoietic stem cell rescue. In such an embodiment, melflufen or a salt thereof, may be administered in a single high dose. A single high dose may be about 150 to 800 mg. For example, 150, 200, 300, 400, 500, 600, 700 and 800 mg.

Melflufen, or a salt thereof, may be administered as a parenteral or oral dosage. In a preferred embodiment of the invention, melflufen or a salt thereof, is administered as a parenteral dosage. As such, pharmaceutical formulations suitable for use according to the invention are those suitable for parenteral administration.

Parenteral administration includes intravenous (into a vein, for example a central or a peripheral vein, bolus or infusion), intra-arterial (into an artery, for example a central or a peripheral artery), intraosseous infusion (into the bone marrow), intra-muscular (into muscle), intradermal (into the dermis), and subcutaneous (under the skin) administration. Preferably, the dosage of the present invention is administered intravenously or intra-arterially, and more preferably by intravenous infusion (for example central intravenous infusion or peripheral intravenous infusion). As such, pharmaceutical formulations especially useful for the present invention are those suitable for intravenous administration, and more especially intravenous infusion.

In one embodiment of the invention, the dosage of melflufen (excluding the mass of any counterion) is administered as a parenteral dosage at an infusion rate of around 1.0 to 1.8 mg/min, for example 1.0 to 1.7 mg/min, 1.0 to 1.6 mg/min, 1.2 to 1.6 mg/min, 1.2 to 1.5 mg/min, 1.2 to 1.4 mg/min (for example 1.2, 1.3 or 1.4 mg/min).

In a preferred embodiment of the invention, the dosage of melflufen of around 35 to 45 mg (excluding the mass of the counterion) is administered as a parenteral dosage over around 25-35 minutes. Preferably, the dosage of melflufen of 40 mg (excluding the mass of the counterion) is administered as a parenteral dosage over around 30 minutes.

In another embodiment of the invention, the dosage of melflufen of around 15 to 25 mg (excluding the mass of the counterion) is administered as a parenteral dosage over around 8-25 minutes, preferably 11 to 18 minutes. Preferably, the dosage of melflufen of 20 mg (excluding the mass of the counterion) is administered as a parenteral dosage over around 15 minutes.

In another embodiment of the invention, the dosage of melflufen of around 25 to 35 mg (excluding the mass of the counterion) is administered as a parenteral dosage over around 16-35 minutes, preferably 18 to 25 minutes. Preferably, the dosage of melflufen of 30 mg (excluding the mass of the counterion) is administered as a parenteral dosage over around 22 minutes.

In another embodiment of the invention, the dosage of melflufen of around 20 to 40 mg (excluding the mass of the counterion) is administered as a parenteral dosage over around 25-35 minutes. Preferably, the dosage of melflufen of 20, 30 or 40 mg (excluding the mass of the counterion) is administered as a parenteral dosage over around 30 minutes.

In another embodiment of the invention, the dosage of melflufen of around 15 to 25 mg (excluding the mass of the counterion) is administered as a parenteral dosage over around 25-35 minutes, preferably 11 to 18 minutes. Preferably, the dosage of melflufen of 20 mg (excluding the mass of the counterion) is administered as a parenteral dosage over around 30 minutes.

In another embodiment of the invention, the dosage of melflufen of around 25 to 35 mg (excluding the mass of the counterion) is administered as a parenteral dosage over around 25 to 35 minutes, preferably 18 to 25 minutes. Preferably, the dosage of melflufen of 30 mg (excluding the mass of the counterion) is administered as a parenteral dosage over around 30 minutes.

As regards the dosage of melflufen for use in the present invention, when a mass of melflufen or a salt thereof is referred to, that is the mass when no counterion is included in the calculation of the dosage mass of the melflufen. The molecular weight of counterion-free melflufen is 498.42 g/mol. For a dosage of a salt of melflufen, the actual dosage mass administered to the patient must take into account the mass of the counterion. This is routine for the person skilled in the art.

For example, when the melflufen is in the form of its hydrochloride (HCl) salt (which has a molecular weight of 534.88 g/mol), the equivalent dosage rate for melflufen hydrochloride (including the mass of the counterion) will be 1.1 to 1.9 mg/min. For a dosage of melflufen of 35 to 40 mg, the equivalent dosage of melflufen hydrochloride will be approximately 37.6 to 48.3 mg.

The dosage regime of the present invention is administered as a parenteral dosage, and thus the dosage of melflufen must be in the form of a liquid, for example a solution or suspension comprising the melflufen.

Preferably the melflufen, or salt thereof, of the present invention is taken as part of a treatment cycle. In a cycle, the melflufen may be administered on day 1 of the cycle, wherein the cycle lasts X days, with no further melflufen administered for the next X−1 days. X may be, for example, from 14 to 42, preferably from 14 to 35 days, and more preferably from 21 to 28 days; for example 21 days or 28 days.

In a preferred embodiment of the invention, melflufen, or a salt thereof, is administered on day 1 of a 21 day cycle followed by 20 days of rest with no further melflufen being administered during that time; or administered on day 1 of a 28 day cycle followed by 27 days of rest with no further melflufen being administered during that time. Preferably the treatment cycle is 28 days.

The cycle may be repeated one or several times depending on the category, class or stage of the AL amyloidosis. For example, the cycle may be repeated from 1 to 15 times, for example from 2 to 12 times, for example 2 to 7 times, for example 2, 3, 4, 5, 6 or times. The cycle may be repeated, 3, 4 or 5 times.

An ordinarily skilled physician or clinician can readily determine the number of cycles of melflufen, or a salt thereof, required to prevent, counter or arrest the progress of the AL amyloidosis.

The dosage regimens of the invention are particularly safe and effective for the treatment and/or prophylaxis of AL amyloidosis in patients with AL amyloidosis or at risk of developing AL amyloidosis.

Whilst melflufen, or a salt thereof, may be used as the sole active ingredient in the present invention, it is also possible for it to be used in combination with one or more further therapeutic agent(s), and the use of such combinations provides one preferred embodiment of the invention. Such further therapeutic agents may be agents useful in the treatment and/or prophylaxis of AL amyloidosis, or other pharmaceutically active materials. Such agents are known in the art. Examples of further therapeutic agents for use in the present invention include steroids (prednisone, prednisolone and dexamethasone), IMiDs (thalidomide, lenalidomide and pomalidomide), PIs (bortezomib, carfilzomib and ixazomib), histone deacetylase (HDAC) inhibitors (panobinostat), conventional chemotherapy (alkylators (e.g. melphalan, cyclophosphamide, bendamustine), doxorubicin), anti-CD38 antibodies (daratumumab) and anti-SLAMF7 antibodies (elotuzumab); for example steroids (prednisone and dexamethasone), IMiDs (thalidomide, lenalidomide and pomalidomide), PIs (bortezomib and carfilzomib), histone deacetylase (HDAC) inhibitors (panobinostat) and conventional chemotherapy (alkylators (e.g. melphalan, cyclophosphamide and doxorubicin)).

The one or more further therapeutic agent(s) may be used simultaneously, sequentially or separately with/from the administration of the dosage of the melflufen, or salt thereof. The individual components of such combinations can be administered separately at different times during the course of therapy or concurrently in divided or single combination forms.

In one embodiment of the invention, at least one of the one or more further therapeutic agent(s) is a steroid. For example, prednisone, prednisolone and dexamethasone. Preferably, at least one of the one or more further therapeutic agent(s) is dexamethasone.

The simultaneous, sequential or separate administration of a steroid such as dexamethasone, with melflufen further enhances the effectiveness of melflufen in treating AL amyloidosis.

In embodiments of the invention where the further therapeutic agent is dexamethasone, preferably the dose of dexamethasone is from 1 mg to 200 mg, preferably 5 mg to 100 mg, more preferably 10 mg to 80 mg, and most preferably 20 mg to 60 mg, for example 20, 30, 40, 50 and 60 mg. Preferably, the dexamethasone is administered as an oral dose or an intravenous dose. More preferably, the dexamethasone is administered as an oral dose.

Preferably, the dexamethasone is administered on the same day as the administration of the melflufen. For example, the dexamethasone is administered on the same day simultaneously, sequentially or separately from administration of the melflufen. More preferably it is administered separately from and on the same day as the melflufen.

For example, when the melflufen, or a salt thereof, for use in the present invention is taken as part of a treatment cycle (for example melflufen, or a salt thereof is administered on day 1 of a cycle lasting X days, with no further melflufen taken for the next X−1 days), the dexamethasone may be administered simultaneously, sequentially or separately on the same day as the melflufen is administered (i.e. on day 1). X may be, for example, from 14 to 42, preferably from 14 to 35 days, and more preferably from 21 to 28 days; for example 21 days or 28 days.

In one embodiment of the invention, melflufen is administered on day 1 of a 21 day cycle, and dexamethasone is administered simultaneously, sequentially or separately on day 1 of the cycle, followed by 20 days of rest with no further melflufen being administered during that time; or administered on day 1 of a 28 day cycle, and dexamethasone is administered simultaneously, sequentially or separately on day 1 on the cycle, followed by 27 days of rest with no further melflufen being administered during that time.

In one embodiment of the invention dexamethasone is administered on day 1 in a treatment cycle, followed by one or more further dose(s) of dexamethasone administered on days 1, 2, 3, 4, 5, 6, 7 and/or 8 of a cycle lasting X days, for example a cycle lasting 21 days or 28 days.

In embodiments of the invention where one or more further dose(s) of dexamethasone are administered during such a treatment cycle, the further doses of dexamethasone may independently be 1 mg to 200 mg, for example 5 mg to 100 mg, 10 mg to 80 mg, and 20 mg to 60 mg (for example 20, 30, 40, 50 and 60 mg). Preferably, the further one or more dose(s) of dexamethasone are administered as an oral dose or an intravenous dose.

In one preferred embodiment of the invention, the dexamethasone is administered simultaneously, sequentially or separately from the melflufen on day 1, followed by a second separate dose of dexamethasone on day 2 of a cycle lasting X days. For example, melflufen is administered on day 1 of a 28 day cycle, followed by 27 days of rest with no further melflufen being administered during that time, and dexamethasone is administered simultaneously, sequentially or separately on day 1 on the cycle, followed by a second separate dose on day 2 of the 28 day cycle.

For example, 40 mg of dexamethasone is administered simultaneously, sequentially or separately from the melflufen on day 1, followed by a second separate dose of 40 mg dexamethasone on day 2 of a cycle lasting X days. For example, 20 to 40 mg (for example, 20, 30 or 40 mg) melflufen is administered on day 1 of a 28 day cycle, followed by 27 days of rest with no further melflufen being administered during that time, and 40 mg dexamethasone is administered simultaneously, sequentially or separately on day 1 on the cycle, followed by a second separate 40 mg dose on day 2 of the 28 day cycle.

The cycle may be repeated, one or several times, depending on the category, class or stage of the AL amyloidosis. For example, the cycle may be repeated from 1 to 15 times, for example from 2 to 12 times, 1 to 9 times, and 2 to 7 times (for example 2, 3, 4, 5, or 6 times).

An ordinarily skilled physician or clinician can readily determine the number of cycles of melflufen, or a salt thereof, required to prevent, counter or arrest the progress of the AL amyloidosis.

Kits

The present invention provides a kit comprising melflufen, or a salt(s) thereof, and one or more further therapeutic agents that are useful in the treatment and/or prophylaxis of AL amyloidosis. Examples of further therapeutic agents for use in the present invention include steroids (prednisone, prednisolone and dexamethasone), IMiDs (thalidomide, lenalidomide and pomalidomide), PIs (bortezomib, carfilzomib and ixazomib), histone deacetylase (HDAC) inhibitors (panobinostat), conventional chemotherapy (alkylators (e.g. melphalan, cyclophosphamide, bendamustine), doxorubicin), anti-CD38 antibodies (daratumumab) and anti-SLAMF7 antibodies (elotuzumab); for example steroids (prednisone and dexamethasone), IMiDs (thalidomide, lenalidomide and pomalidomide), PIs (bortezomib and carfilzomib), histone deacetylase (HDAC) inhibitors (panobinostat) and conventional chemotherapy (alkylators (e.g. melphalan, cyclophosphamide and doxorubicin).

In a preferred embodiment of the invention, at least one of the one or more further therapeutic agent(s) included in the kit of the invention is a steroid. Preferably, the steroid is selected from prednisone, prednisolone and dexamethasone. More preferably the steroid is dexamethasone.

In one embodiment of the invention, the kit of the present invention finds use in the treatment and/or prophylaxis of AL amyloidosis.

For the avoidance of doubt, the melflufen, or salt thereof, is present in a kit according to the present invention in a form and quantity suitable for use according to the present invention. Suitable pharmaceutical formulations are described herein. The skilled person can readily determine a quantity of the melflufen, or a salt thereof, suitable for the use according the present invention.

AL Amyloidosis Patients

Melflufen, or a salt(s) thereof, for use according to the invention, is useful for the treatment of AL amyloidosis that may be classed as refractory, relapsed and refractory-relapsed AL amyloidosis.

Relapsed AL amyloidosis can be defined as AL amyloidosis that recurs following the last dosage of treatment. Refractory AL amyloidosis can be defined as AL amyloidosis that is not responsive to currently available treatments. Refractory-relapsed AL amyloidosis can be defined as AL amyloidosis that initially responds to treatment, but does not respond to treatment after relapse.

Melflufen, or a salt thereof, finds use in the treatment of refractory, relapsed and/or refractory-relapsed AL amyloidosis. For example, melflufen finds use in the treatment and/or prophylaxis of refractory, relapsed and/or refractory-relapsed AL amyloidosis in patients that have previously been treated with a currently available treatment, such as single or repeat treatment cycles of melphalan, melphalan and dexamethasone, and/or high-dose melphalan and haematopoietic stem cell rescue.

Thus, in one embodiment of the invention, melflufen, or a salt thereof, finds use in the treatment and/or prophylaxis of immunoglobulin light chain (AL) amyloidosis in patients with refractory, relapsed and/or refractory-relapsed AL amyloidosis.

Melflufen, or a salt(s) thereof, finds use in the prophylaxis of AL amyloidosis in patients that have a known or suspected risk of developing AL amyloidosis. Such patients include but are not limited to those having chronic inflammatory diseases, inherited inflammatory diseases, and chronic microbial infections, for example, rheumatoid arthritis, juvenile chronic arthritis, ankylosing spondylitis, psoriasis, psoriatic arthropathy, Reiter's syndrome, Adult Still's disease, Behcet's syndrome, Crohn's disease, Familial Mediterranean Fever, leprosy, tuberculosis, bronchiectasis, decubitus ulcers, chronic pyelonephritis, osteomyelitis, Whipple's disease, myeloma, macroglobulinemia, immunocyte dyscrasia, monoclonal gammopathy, occult dyscrasia.

Melflufen, or a salt(s) thereof, also finds use in the treatment of AL amyloidosis patient groups considered to be a "high risk" group that may not tolerate or respond positively to existing AL amyloidosis treatments. High risk patients include, for example, patients who have poor general well-being and quality of life (measured, for example by the Karnofsky score, Lansky score, and/or the Eastern Cooperative Oncology Group (ECOG) score), cardiac disease, salt and water retention, amyloid-related autonomic neuropathy, and/or liver dysfunction.

The present inventors postulate that the surprisingly high potency of melflufen will enable the effective treatment of AL amyloidosis patient groups that have not responded to existing AL amyloidosis treatments or that are considered unsuitable for existing AL amyloidosis treatments, for example patients having refractory and/or relapsed AL amyloidosis, and AL patients who are categorised, for example, as "high-risk" AL amyloidosis patients.

The following Examples illustrate the invention.

EXAMPLES

Example 1: Cytotoxicity of Melflufen Towards Plasma Cells Derived From AL Amyloidosis Patients Materials and Methods Patient Derived Mononuclear Cells Viably frozen bone marrow mononuclear cells (MNC) from 11 amyloidosis patients were received from a biobank.

Cell Culture and Assay Conditions

Viably frozen cells were thawed and incubated overnight to exclude apoptotic cells. On Day 1, a homogeneous cell suspension at a density of $2 \times 10^6$ cells/ml was prepared in RPMI 1640 medium (Lonza) supplemented with 10% fetal bovine serum, 2 mM L-glutamine, penicillin (100 U/ml), streptomycin (100 µg/ml) and 25% conditioned medium from the HS-5 human BM stromal cell line. Melflufen powders were stored in pre-weighted amounts in vials in oxygen and moisture free storage pods. Fresh 10 mM melflufen aliquots were prepared in DMSO. Serial dilutions were prepared in cell culture media and immediately transferred to 96 well plate containing mononuclear cells.

Multiplexed High Throughput Flow Cytometry

A multiplexed high throughput flow cytometer based assay (iQue® Screener PLUS) was applied, allowing simultaneous monitoring of drug responses in multiple hematopoietic cell subsets. A panel of eight antibodies against CD8, CD14, CD19, CD38, CD45, CD56, CD138 and CD269 were purchased. Annexin-V and 7-AAD were included to exclude dead or apoptotic cells from the analysis. Optimal antibody concentrations were determined and fluorescence compensations were computed to correct spectral overlaps between different fluorochromes. The plates containing melflufen treated cells were incubated in a humidified environment at 37° C. and 5% $CO_2$. After 72 h, antibody cocktails were added to the wells and incubated for 30 min before the plates were read with the iQue® Screener PLUS instrument (Intellicyt®). The data was analyzed using ForeCyt software (Intellicyt). Graphpad Prism 7.0 to generate dose response graphs. Singlet mononuclear cells were subjected to dead and apoptotic cell exclusion using DNA staining dye 7-AAD and expression of Annexin-V surface antigens. Live cell counts for each cell populations were used to analyse effect of different doses on cell viability. Surviving cell fraction were computed by normalizing with viability of untreated cells for each cell subsets.

Melflufen was tested in six concentration over 100,000-fold dilutions (1 to 100,000 nM). Out of 12 cell samples tested, two samples were excluded due to poor viability. The viable samples were assigned the reference numbers AL-1886, AL-2983, AL-4839_2, AL-4839_3, AL-4847, AL-5691, AL-5716, AL-5807, AL-7219, AL-400081.

Figure 1:
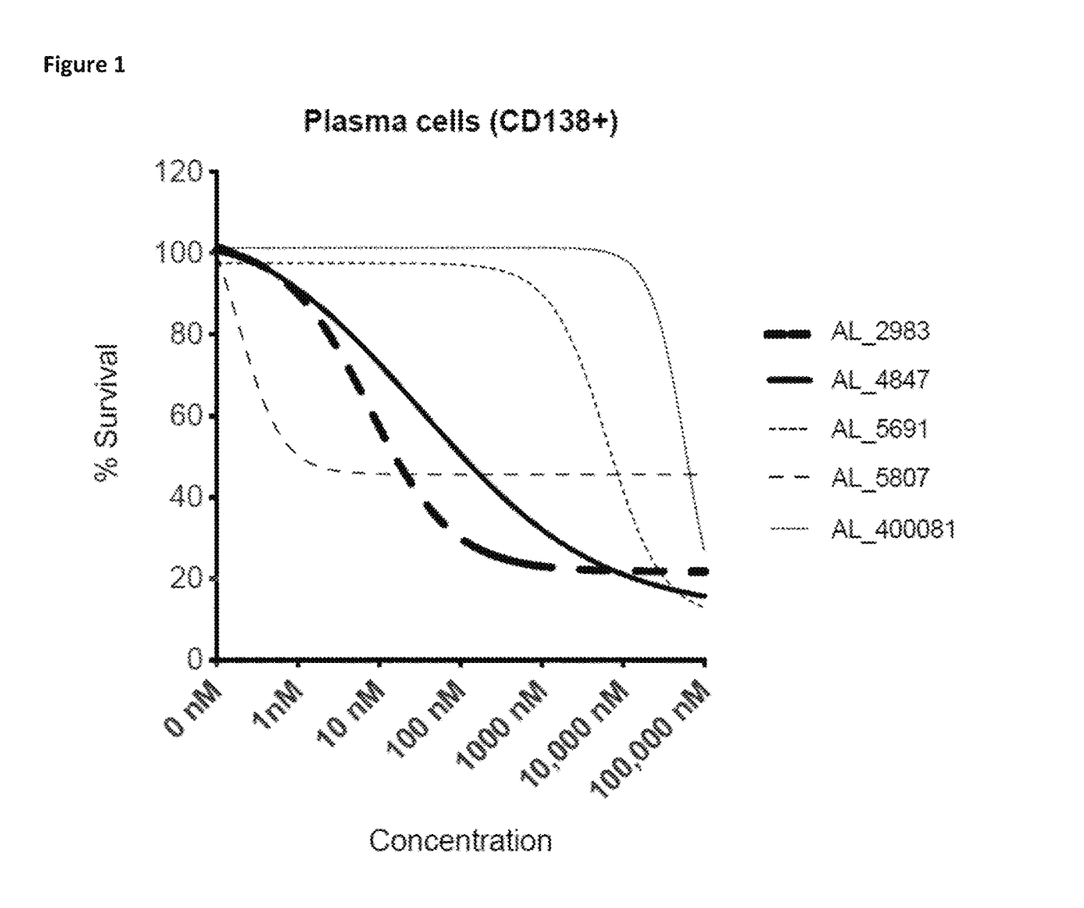
FIG. 1 shows the percentage survival of the plasma cells (CD138$^+$ cells) within bone marrow mononuclear cell samples (AL-2983, AL-4847, AL-5691, AL-5807 and AL-400081) following treatment with melflufen.
Figure 2:
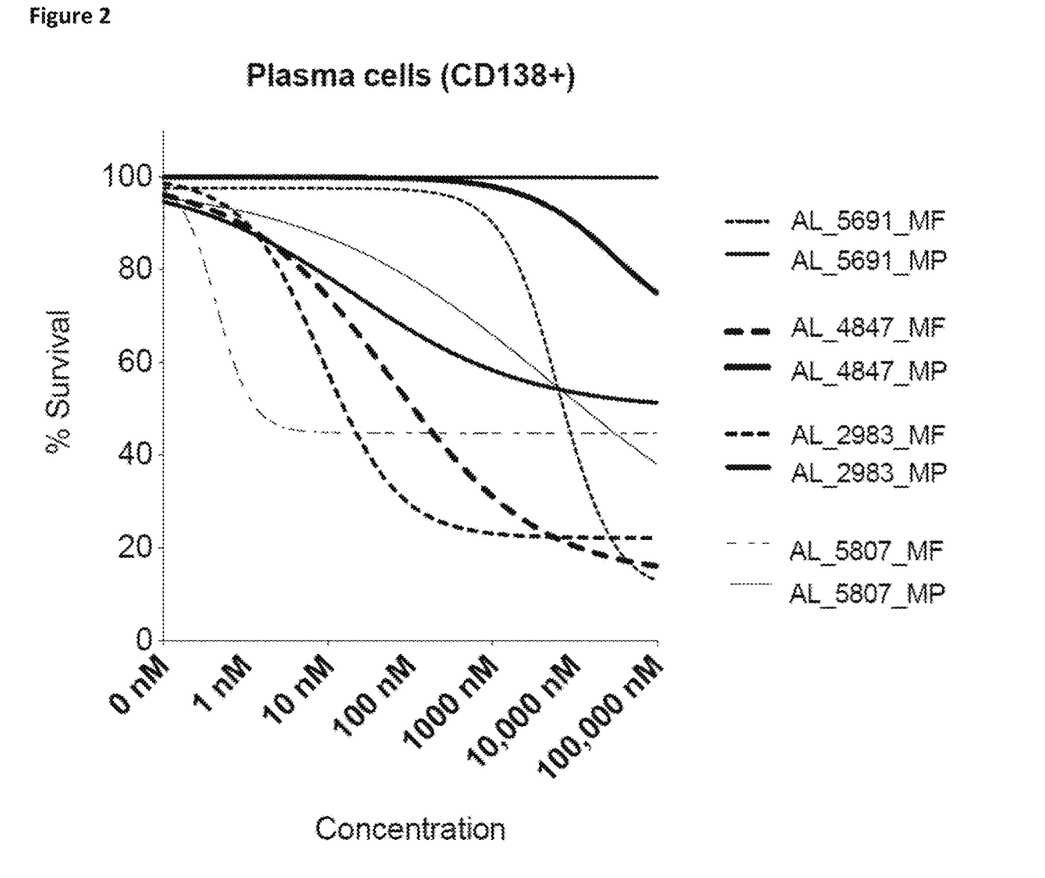
FIG. 2 shows the percentage survival of the plasma cells (CD138$^+$ cells) within bone marrow mononuclear cell samples AL-5691, AL-4847, AL-2983, and AL-5807 following treatment with melflufen (MF) or melphalan (MP).

The plasma cells (CD138$^+$ cells) of samples AL-2983, AL-4847, AL-5691, AL-5807 and AL-400081 displayed sensitivity to melflufen (FIG. 1). Notably, an $EC_{50}$ of 1 nM was observed for AL-5807, an $EC_{50}$ of 7 nM was observed for AL-2983, and an $EC_{50}$ of 32 nM was observed for AL-4847. Plasma cells of samples AL-1886, AL-4839_2, AL-4839_3, AL-5716 and AL-7219 showed no notable response to melflufen. For comparative purposes, melphalan was tested in identical concentrations for each of the cell samples. Melflufen was found to be 100 times more cytotoxic compared to melphalan (FIG. 2).

Example 2: Cellular Toxicity Response to Melflufen or Melphalan in Amyloidosis Patient-Derived Light Chain Secreting Cell Lines Cellular toxicity was measured in response to either melflufen or melphalan in the amyloidosis patient-derived light chain secreting ALMC-1 and ALMC-2 cell lines, and the light chain secreting cell line JJN3.

Cells were plated in a 96-well format in the presence of the indicated compound in doses ranging from 0.014 to 10 mM for 72 hours at 37° C. Cell viability was determined by CellTiter-Blue™ using the manufacturer's standard protocol. Lambda and kappa light chain secretion was measured in the supernatant of cells by ELISA.

In more detail, for each cell line (JJN3, ALMC-1 and ALMC-2) cells were harvested, washed, re-suspended into full growth media and counted. The growth media used for each cell line is shown in Table 1, below. The cells were seeded at the cell densities shown in Table 1, below, into the inner 60 wells of a 96-well assay plates (Corning, black-wall plates, Cat #3904) in 50 µl/well aliquots. The plates were incubated overnight at 37° C. in 5% humidified $CO_2$. 10 mM stocks of melphalan or melflufen-HCl were used, and sub-aliquots were prepared from the 10 mM stocks of melphalan or melflufen-HCl by diluting the stock. The diluted stock was added into cell culture media at the indicated concentrations for the experiment (0.014 to 10 mM).

50 microliters per well of compound/vehicle dilutions were added to the plates in replicates of 3 and incubated for 72 h at 37° C. in 5% humidified $CO_2$. To develop the plates after 72 h, 20 µl of CellTiter-Blue™ reagent was added to each test/blank well. The plates were incubated at 37° C., 5% humidified $CO_2$ for 1.5/3 h. Fluorescence was measured using a VarioSkan Flash plate reader (570 nm excitation wavelength, 600 nm emission wavelength).

For analysis of secreted proteins, 72 h after incubation, the cells were pelleted by centrifugation at 300 RCF, 4° C. for 5 min and the supernatant taken and used immediately for ELISA analysis using commercial ELISA kits (below) and the manufacturer's protocols:

Human Kappa ELISA (Bethyl Laboratories, #E80-115)
Human Lambda ELISA (Bethyl Laboratories, #E80-116)

TABLE 1

| Cell line | Culture media | Incubation time (h) | Cell density (cell/ml) | Cell density (cells/well) in 50 µl |
|---|---|---|---|---|
| JJN3 | 40% Iscove's Modified Dulbecco's Medium (Sigma, I3390), 40% DMEM (Sigma, D5671) + 20% FBS (Sigma, F7524) + 2 mM L-Glutamine (Sigma, 59202C) | 72 | 125,000 | 6,250 |
| ALMC1 | 40% Iscove's Modified Dulbecco's Medium (Sigma, I3390) + 10% FBS (Sigma, F7524) + 2 mM L-Glutamine (Sigma, 59202C) + 1 ng/ml IL-6 and 10 ng/ml EGF | 72 | 500,000 | 25,000 |
| ALMC2 | 40% Iscove's Modified Dulbecco's Medium (Sigma, I3390) + 10% FBS (Sigma, F7524) + 2 mM L-Glutamine (Sigma, 59202C) + 1 ng/ml IL-6 and 10 ng/ml EGF | 72 | 500,000 | 25,000 |

Figure 3:
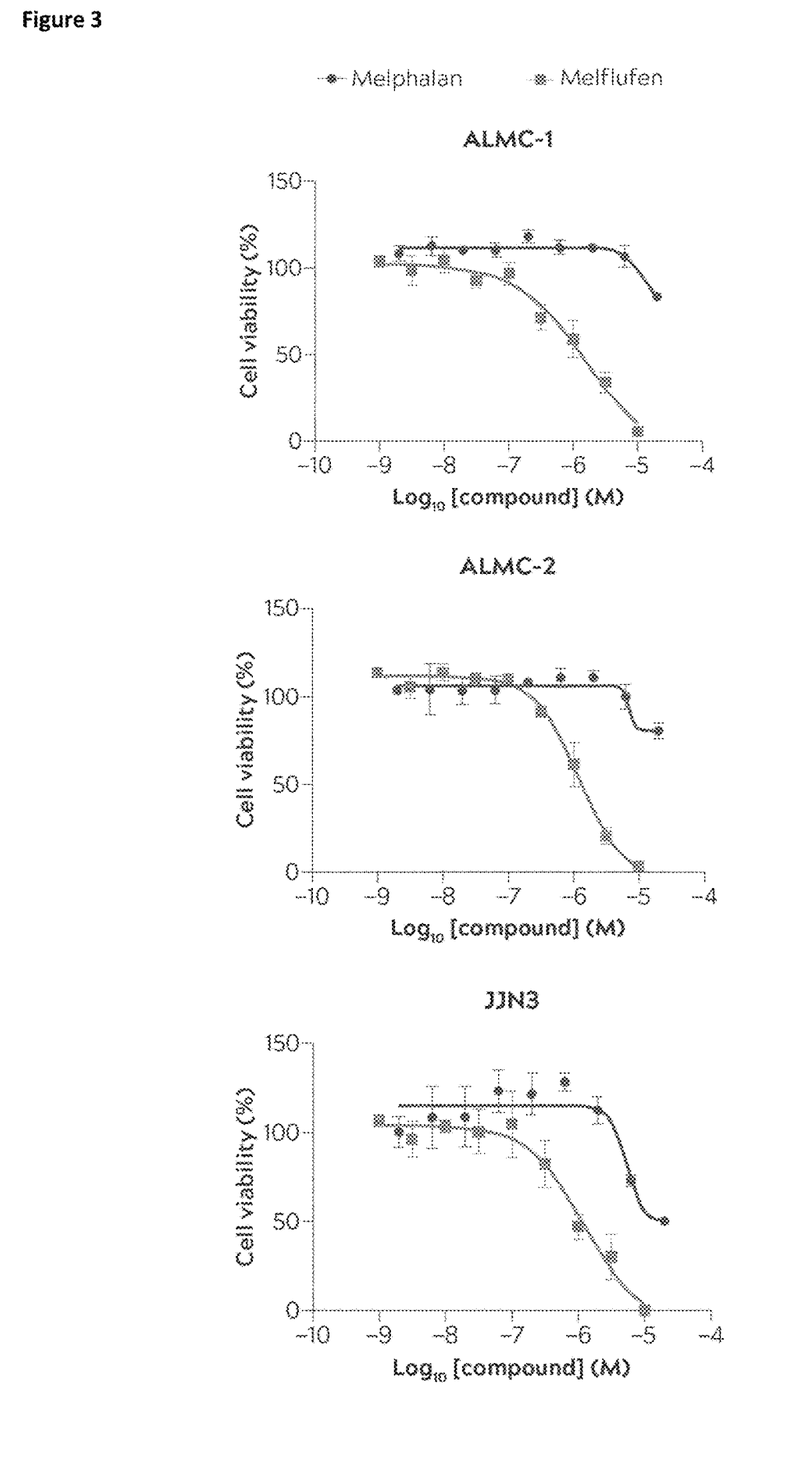
FIG. 3 shows melflufen-mediated and melphalan-mediated sensitivity in three light chain producing plasma cell lines (JJN3, ALMC-1 and ALMC-2).
Figure 4:
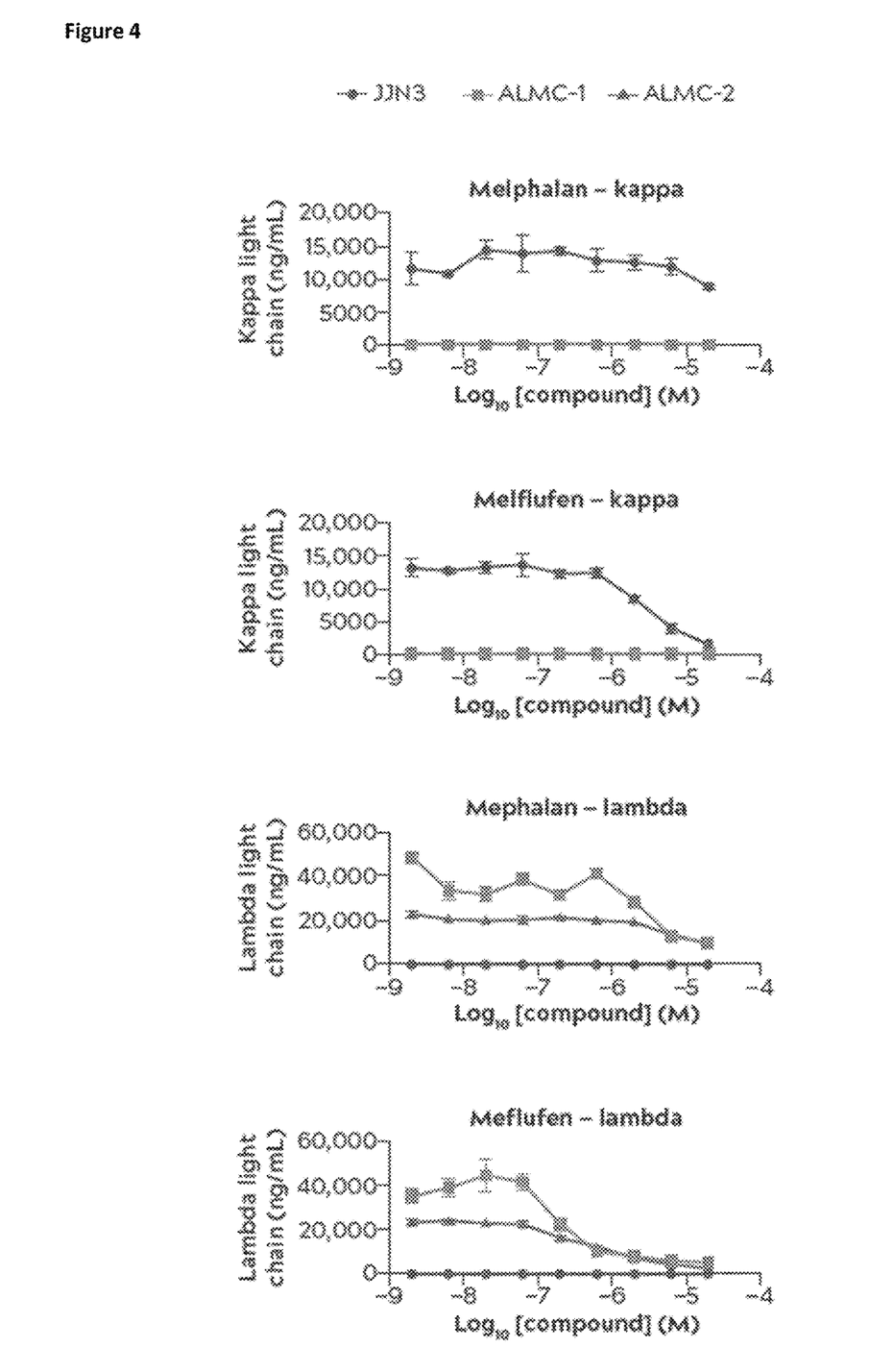
FIG. 4 shows melflufen-mediated and melphalan-mediated reduction in kappa or lambda light chain secretion in three light chain producing plasma cell lines (JJN3, ALMC-1 and ALMC-2).

Results:

FIG. 3 shows the melflufen-mediated and melphalan-mediated sensitivity in the three light chain producing plasma cell lines. Table 2 below shows the $IC_{50}$ values for melflufen and melphalan in each of the three light chain producing plasma cell lines. FIG. 4 shows the melflufen-mediated and melphalan-mediated reduction in light chain secretion in the three light chain producing plasma cell lines. Table 3 below shows the Human Lambda ELISA results for melflufen and melphalan in the ALMC-1 and ALMC-2 cell lines. Table 4 below shows the Human Kappa ELISA results for melflufen and melphalan in the JJN3 cell line.

As can be seen from FIG. 3 and Table 2, all three light chain secreting cell lines (JJN3, ALMC-1 and ALMC-2) tested demonstrated increased sensitivity to melflufen compared with melphalan. As can be seen from FIG. 4 and Tables 3 and 4, melflufen also demonstrated superior inhibition of light chain secretion compared to melphalan in all three light chain secreting cell lines. Therefore, the results show that melflufen demonstrated superior efficacy in amyloidogenic plasma cell lines compared with melphalan, with increased plasma cell death and decreased secretion of light chains

TABLE 2

| | ALMC-1 $IC_{50}$ (µM) | ALMC-2 $IC_{50}$ (µM) | JJN3 $IC_{50}$ (µM) |
|---|---|---|---|
| melphalan | — | — | 5.4 |
| melflufen | 1.6 | 1.2 | 1.2 |

TABLE 3

|  | ALMC-1 IC$_{50}$ (μM) | ALMC-2 IC$_{50}$ (μM) |
|---|---|---|
| melphalan | 2.5 | 5.1 |
| melflufen | 0.20 | 0.45 |

TABLE 4

|  | JJN3 IC$_{50}$ (μM) |
|---|---|
| melphalan | — |
| melflufen | 2.9 |

Example 3: Effects of Melflufen on Apoptosis and Markers of Unfolded Protein Response (UPR)

The toxic effects of melflufen and melphalan were compared in malignant cell lines, including RPMI-8826, ALMC-2, MM1S, and U266 to confirm enhanced toxicity of melflufen compared to melphalan. ALMC-2 cells are derived from an amyloidosis patient. MM1S, RPMI-8826, U266 or ALMC-2 cells were incubated in the presence or absence of melflufen-HCl or melphalan at the indicated concentrations in FIG. 5A for 6 h, 12 h or 24 h. Cells were then harvested and apoptosis and cell death in response to melflufen and melphalan were measured by Annexin V/propidium iodide and live/dead cell staining by flow cytometry, as well as analysis of cleaved caspases 3, 8, and 9 and PARP by western blot. Effects of melflufen and melphalan on the UPR were examined by analysis of UPR associated molecules including phosphorylated eIF2a, ATF4, IRE1a and PERK by immunoblot analysis using commercially available detection reagents and standard protocols, and ATF4, ATF6, PERK, IRE1 and CHOP by real time qPCR with gene specific primer sets. In addition, XBP-1 splicing was evaluated by PCR analysis.

Figure 5:
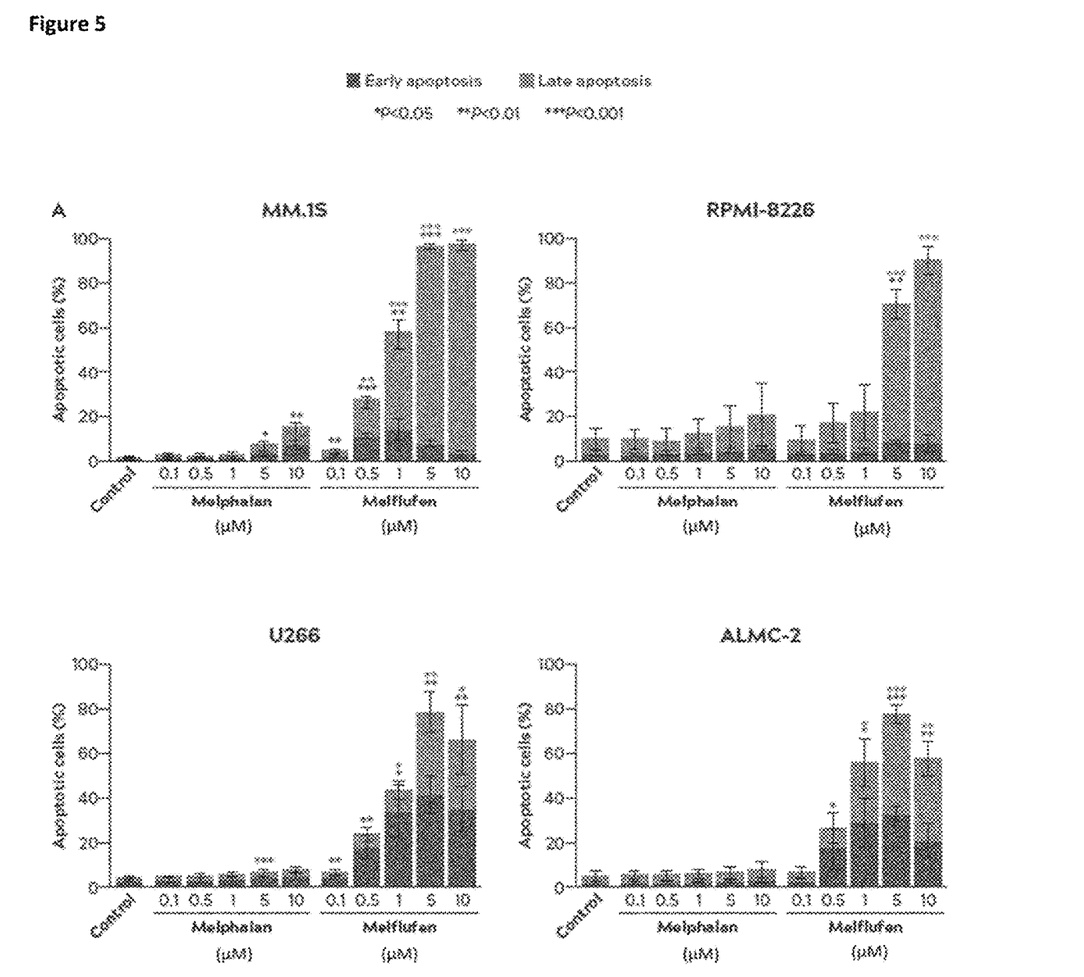
FIG. 5A shows % apoptotic cells in 4 cells lines (MM.1S, RPMI-8826, U266 and ALMC-2) after treatment with varying concentrations of melflufen or melphalan (*p<0.5, p<0.01, *p<0.001).
FIG. 5B shows results of XBP-1 splicing by PCR in 4 cells lines (MM.1S, RPMI-8826, U266 and ALMC-2) at 12 hours after treatment with varying concentrations of melflufen or melphalan.
FIG. 5C shows results of the UPR and apoptosis marker immunoblot (western blot) analysis for multiple time points (6 h, 12 h and 24 h) after treatment with varying concentrations of melflufen or melphalan.

Results:

Results of analysis for Annexin V/propidium iodide by flow cytometry are shown in FIG. 5A (early apoptotic cells are positive for Annexin V, late apoptotic cells are positive for both), results of XBP-1 splicing by PCR are shown in FIG. 5B, and the results of the UPR and apoptosis marker immunoblot analysis by western blot are shown in FIG. 5C for multiple time points (6 h, 12 h and 24 h).

As can be seen from the results in FIGS. 5A to 5C, all cell lines tested were significantly more sensitive to melflufen than melphalan with regard to inducing apoptosis, stimulating endoplasmic reticulum stress as indicated by XBP-1 splicing, as well as stimulation of multiple markers of UPR and apoptosis. Therefore, these results show that melflufen demonstrated significant effects on apoptosis, with increased induction of apoptotic and UPR markers in comparison with melphalan.

Example 4: Human Plasmacytoma Xenograft Mouse Study to Test the Efficacy of Melflufen in a Model of Amyloidosis A xenograft model to assess the efficacy of melflufen for the treatment of amyloidosis was established. The light chain secreting human myeloma cell line, JJN3, which is sensitive to melflufen ex vivo as shown by the result of Example 3, above, was transduced with luciferase and adoptively transferred into NSG mice. The model is used to analyze the in vivo effects of melflufen on both amyloidogenic plasma cell toxicity (measured by in vivo bioluminescence) and serum levels of B cell maturation antigen (BCMA) and light chains.

Xenograft Model

JJN3 human myeloma cells were stably transduced with the firefly luciferase gene using standard protocols (Brennan et al., Bio Protoc. 2018; 8(8): e2817). 5 female NSG mice received an intraperitoneal (i.p.) injection of cell suspension of the resulting JJN3-luciferase cells into the peritoneal cavity at $1 \times 10^7$ cells per mouse. Mice were observed by an experienced technician at least once daily, for physical appearance, behavior and clinical changes. Mice were weighed three times per week for the duration of the study (16 days). Tumour growth was checked once or twice weekly (for example at day 6, 9, 13 and 16 after tumor inoculation) by bioluminescent imaging (BLI). Briefly, the mice were injected subcutaneously (s.c.) with 150 mg/kg d-Luciferin 15 minutes prior to imaging. 10 minutes following administration of d-Luciferin mice were anaesthetised and placed into the imaging chamber (Spectrum CT) and imaged for luminescence (ventral view/dorsal/left lateral, covering the tail with black straw; up to 5 mice laid alongside each other in cage order). The order and positioning remained constant throughout the study. Duration and binning (sensitivity) of the image acquisition was dependent upon the intensity of the lesions present and was captured and processed using Living Image software (Caliper LS, US). Levels of kappa and lambda light chains as well as BCMA from the serum was analysed on days 9 and 16 post tumor inoculation using commercial ELISA kits (below) and manufacturer's protocols:

Human Kappa ELISA (Bethyl Laboratories, #E80-115)
Human Lambda ELISA (Bethyl Laboratories, #E80-116)
Human BCMA ELISA (R&D Systems, #DY193).

Figure 6:
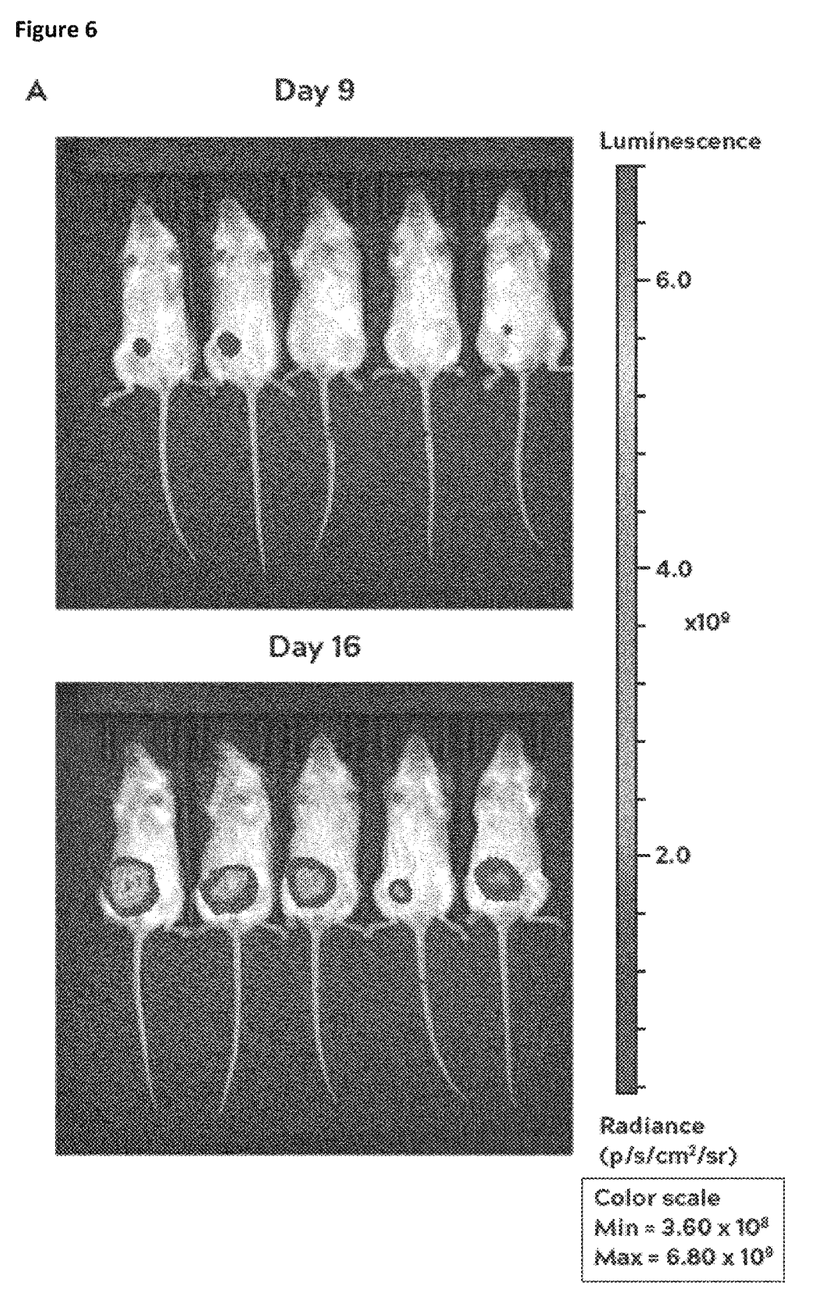
FIG. 6A shows in vivo bioluminescent imaging of 5 mice following luciferin administration on days 9 and 16 after tumor inoculation.
FIG. 6B shows the level of lucerifase radiance (photons per second (p/s)) in 5 mice as measured ventrally, dorsally, or averaged ventral and dorsal results, on days 6, 9, 13 and 16 after tumor inoculation.

Results:

The results of in vivo bioluminescent imaging following luciferin administration for 5 mice on days 9 and 16 after tumor inoculation is shown in FIG. 6A, and the level of lucerifase radiance (photons per second (p/s)) as measured ventrally, dorsally, or averaged ventral and dorsal results, on days 6, 9, 13 and 16 after tumor inoculation in each mouse is shown in FIG. 6B. Table 5, below, shows the serum levels of BCMA and kappa and lambda light chains monitored by ELISA on a day after tumor inoculation, as well as tumor burden by bioluminescent imaging in each mouse.

As can be seen from FIGS. 6A and 6B and Table 5, row 3, JJN3 tumors were detectable in all inoculated mice, with variable tumor burden. As shown in Table 5, rows 1 and 2, BCMA and kappa light chains were detectable in the serum of 3/5 mice, which corresponded to the mice with the greatest detected tumor burden. These results show that an animal model using transfer of amyloidogenic plasma cells that are sensitive to melflufen ex vivo has been established and can be used to analyze the in vivo effects of melflufen on both amyloidogenic plasma cell toxicity and serum levels of BCMA and light chains.

TABLE 5

| | | | | | |
|---|---|---|---|---|---|
| BCMA (pg/mL) | 855 | 2303 | 686 | 0 | 0 |
| Kappa light chain (pg/mL) | 742 | 2431 | 987 | 0 | 0 |
| Tumor burden (BLI) | $6.02 \times 10^8$ | $7.63 \times 10^8$ | $5.51 \times 10^8$ | $1.87 \times 10^8$ | $1.01 \times 10^8$ |

Efficacy Study Using Xenograft Model

The xenograft model described above is used to assess efficacy of melflufen in vivo. Melflufen-HCl is administered to 10 NSG mice on, for example, day 0, 2, 4, 6, 8, 10, 12 and 14 following adoptive transfer of JJN3-luciferase cells on day 0, as described above. Cell death in response to melflufen is measured by in vivo bioluminescence as described above on, for example, day 5, 9 and 13, and serum light chain is monitored on, for example, day 7 as described above.

Alternatively, CB17 NOD SCID mice are subcutaneously inoculated into the left hind flank with $1 \times 10^7$ JJN-3 cells in 200 µl of reduced Matrigel under gaseous anaesthesia using a 27 gauge needled following skin disinfection with 70% ethanol. Tumor length (L) and width (W) are monitored using an electronic calliper three times per week. The animals are randomized into three treatment groups (N=10 mice per group) when a mean tumor volume of 100 mm$^3$ is reached (calculated using the formula: $0.5(L \times W^2)$). Upon randomization, either melphalan or melflufen-HCl is dissolved in DMSO to a stock concentration of 6 mg/ml and further diluted 1:20 to experimental concentrations for administration into animals in phosphate buffered saline at a concentration of 3 mg of drug per kg of body weight (with groups receiving melphalan or melflufen-HCl or vehicle control) by intravenous tail vein administration, and dosing is repeated twice per week following the initial dosing, and maintained throughout the study. The animals are monitored 3 times per week for general behaviour and physical condition, tumor growth, and change in body weight. The animals are euthanized if adverse clinical signs developed, body weight is reduced by 20% of original weight, or the tumor volume reaches a mean diameter of 15 mm. Blood samples (<50 µl) are obtained by saphenous vein and processed to serum one day after initiation of dosing, and weekly thereafter, as well as upon termination of the experiment. Serum samples are analysed for light chain concentrations as described herein using commercial Human Kappa, Lambda and BCMA ELISA kits.

Example 5: Treatment of a Patient Suffering from AL Amyloidosis

A patient suffering from AL amyloidosis presents in the clinic, having previously been treated with high-dose melphalan and autologous haematopoietic stem cell rescue. The patient is one who did not experience significant regression of the AL amyloidosis and/or experienced a relapse in the AL amyloidosis. The patient is administered 40 mg melflufen on day 1 of the treatment. Alternatively, the patient is administered 20 mg or 30 mg melflufen on day 1 of the treatment. On day 1 the patient is additionally administered 40 mg or 20 mg of dexamethasone. A second 20 mg or 40 mg dose of dexamethasone is administered on day 2 of the treatment cycle. The dosage of dexamethasone is decided by the clinician based on the particular characteristics of the patient such as the severity of the AL amyloidosis at the start of the treatment cycle and other related physical factors. After 27 days of rest a second 28 day melflufen/dexamethasone treatment cycle may be initiated. Depending on the severity of the AL amyloidosis several treatment cycles may be used.

The invention claimed is:

1. A method for treating a patient having immunoglobulin light chain (AL) amyloidosis, comprising administering melflufen, or a salt thereof, to the patient wherein the melflufen, or a salt thereof, is administered at a dose of about 15 mg to 35 mg excluding the mass of any counterion.

2. The method of claim 1, further comprising administering to the patient simultaneously, sequentially or separately from melflufen, or a salt thereof, a steroid selected from the group consisting of prednisone, prednisolone and dexamethasone.

3. The method of claim 1, wherein a dose of melflufen, or a salt thereof, is administered on day 1 of a cycle of 21 days or a cycle of 28 days.

4. The method of claim 3, wherein the cycle is repeated from 1 to 9 times.

5. The method of claim 3, wherein the cycle is repeated from 2 to 7 times.

6. The method of claim 1, further comprising administering to the subject simultaneously, sequentially or separately from melflufen, or a salt thereof, one or more further therapeutic agent(s).

7. The method of claim 2, wherein the steroid is dexamethasone.

8. The method of claim 7, wherein the dexamethasone is administered at a dose of 1 mg to 200 mg.

9. The method of claim 8, wherein the dexamethasone is administered at a dose of 20 mg, 30 mg or 40 mg.

10. The method of claim 3, wherein a first dose of dexamethasone is administered on day 1 of the cycle, followed by a second dose of dexamethasone on day 2 of the cycle.

11. The method of claim 10, wherein the first dose of dexamethasone is administered at a dose of 1 mg to 200 mg, and the second dose of dexamethasone of is administered at a dose of 1 mg to 200 mg.

12. The method of claim 1, which comprises administering a pharmaceutical formulation comprising melflufen, or a salt thereof.

13. The method of claim 1, wherein the AL amyloidosis is relapsed AL amyloidosis.

14. The method of claim 1, wherein the AL amyloidosis is refractory AL amyloidosis.

15. The method of claim 1, wherein the AL amyloidosis is refractory-relapsed AL amyloidosis.

16. The method of claim 1, wherein the AL amyloidosis is refractory AL amyloidosis or refractory-relapsed AL amyloidosis and is refractory to at least (a) melphalan, (b) melphalan and dexamethasone, and/or (c) melphalan and haematopoietic stem cell rescue.

17. The method of claim 1, wherein melflufen or a salt thereof is administered parenterally.

18. The method of claim 1, wherein the melflufen, or a salt thereof, is administered at a dose of about 20 mg excluding the mass of any counterion.

19. The method of claim 1, wherein the melflufen, or a salt thereof, is administered at a dose of about 30 mg excluding the mass of any counterion.

* * * * *

UNITED STATES PATENT AND TRADEMARK OFFICE
CERTIFICATE OF CORRECTION

PATENT NO. : 12,396,975 B2
APPLICATION NO. : 17/600657
DATED : August 26, 2025
INVENTOR(S) : Jakob Lindberg Page 1 of 1

It is certified that error appears in the above-identified patent and that said Letters Patent is hereby corrected as shown below:

In the Claims

Claim 1, Column 18, Lines 4-6:
"melflufen, or a salt thereof, to the patient wherein the melflufen, or a salt thereof, is administered at a dose of about 15 mg to 35 mg excluding the mass of any counterion."

Should read:
-- melflufen, or a salt thereof, to the patient, wherein the melflufen, or a salt thereof, is administered at a dose of about 15 mg to 35 mg excluding the mass of any counterion. --

Signed and Sealed this
Ninth Day of December, 2025

John A. Squires
*Director of the United States Patent and Trademark Office*